US012806061B2

(12) United States Patent
Armstrong

(10) Patent No.: US 12,806,061 B2
(45) Date of Patent: Nov. 24, 2026

(54) ENDOLUMINAL STOMA DEVICE

(71) Applicant: Armstrong Medical, Inc., Atlanta, GA (US)

(72) Inventor: David N. Armstrong, Atlanta, GA (US)

(73) Assignee: Armstrong Medical, Inc., Atlanta, GA (US)

( * ) Notice: Subject to any disclaimer, the term of this patent is extended or adjusted under 35 U.S.C. 154(b) by 938 days.

(21) Appl. No.: 17/927,439

(22) PCT Filed: May 27, 2021

(86) PCT No.: PCT/US2021/034619

§ 371 (c)(1),
(2) Date: Nov. 23, 2022

(87) PCT Pub. No.: WO2021/243082

PCT Pub. Date: Dec. 2, 2021

(65) Prior Publication Data

US 2023/0218424 A1 Jul. 13, 2023

Related U.S. Application Data

(60) Provisional application No. 63/031,285, filed on May 28, 2020.

(51) Int. Cl.
*A61F 5/441* (2006.01)
*A61F 5/44* (2006.01)
(Continued)

(52) U.S. Cl.
CPC ............ *A61F 5/4407* (2013.01); *A61F 5/441* (2013.01); *A61F 5/442* (2013.01); *A61F 2005/4483* (2013.01)

(58) Field of Classification Search
CPC ........ A61F 5/4407; A61F 5/441; A61F 5/442; A61F 2005/4483
See application file for complete search history.

(56) References Cited

U.S. PATENT DOCUMENTS 4,137,918 A * 2/1979 Bogert .................... A61F 5/445 604/328
5,425,761 A * 6/1995 Lundgren ......... A61M 39/0247 606/155
(Continued)

FOREIGN PATENT DOCUMENTS

EP 2856985 B1 11/2017
GB 1492946 A 11/1977
(Continued)

OTHER PUBLICATIONS

International Search Report for co-pending PCT Patent Application No. PCT/US2021/034619 dated Nov. 4, 2021.
(Continued)

*Primary Examiner* — Guy K Townsend
(74) *Attorney, Agent, or Firm* — Christensen, Fonder Dardi PLLC; Peter S. Dari; Elizabeth A. Gallo

(57) ABSTRACT

A colostomy device, which can be referred to as an endoluminal stoma channel, is provided which incorporates a generally cylindrical membrane, with a ring located at either end: an inner luminal ring which is located within the bowel and an outer ring which is rolled over itself to abut against the skin, to which a colostomy bag may be attached. In a corresponding system (stoma discharge control system), the colostomy device (endoluminal stoma channel) is associated with a cover or cap that can facilitate control of discharge from the stoma, and various cover/cap structures are described. Corresponding methods are described.

9 Claims, 24 Drawing Sheets

(51) Int. Cl.
*A61F 5/442* (2006.01)
*A61F 5/448* (2006.01)

(56) References Cited

U.S. PATENT DOCUMENTS

| | | | | |
|---|---|---|---|---|
| 5,582,577 | A | 12/1996 | Lund et al. | |
| 6,050,982 | A | 4/2000 | Wheeler | |
| 7,662,161 | B2 | 2/2010 | Briganti et al. | |
| 7,736,306 | B2 * | 6/2010 | Brustad | A61B 17/3423 600/233 |
| 8,070,736 | B2 | 12/2011 | Nishtala et al. | |
| 8,740,785 | B2 | 6/2014 | Butler et al. | |
| 8,740,832 | B2 | 6/2014 | Smith et al. | |
| 9,011,395 | B2 | 4/2015 | Friske et al. | |
| 9,649,102 | B2 | 5/2017 | Albrecht et al. | |
| 2006/0149137 | A1 * | 7/2006 | Pingleton | A61B 17/3423 600/208 |
| 2008/0065031 | A1 | 3/2008 | Turner | |
| 2011/0092929 | A1 | 4/2011 | Weig | |
| 2011/0144601 | A1 | 6/2011 | Villefrance et al. | |
| 2013/0060212 | A1 * | 3/2013 | Hanuka | A61F 5/4405 604/333 |
| 2013/0204216 | A1 * | 8/2013 | Matar | A61F 5/448 604/332 |
| 2014/0303443 | A1 * | 10/2014 | Bonadio | A61B 17/3423 600/203 |
| 2015/0164679 | A1 * | 6/2015 | Maidl | A61F 5/445 604/332 |
| 2017/0209297 | A1 | 7/2017 | Lysgaard | |
| 2017/0281397 | A1 | 10/2017 | Davies et al. | |
| 2020/0008792 | A1 | 1/2020 | Becerra et al. | |
| 2023/0218424 | A1 * | 7/2023 | Armstrong | A61F 5/445 604/334 |
| 2024/0122739 | A1 * | 4/2024 | Vella | A61F 5/445 |
| 2025/0228696 | A1 * | 7/2025 | Armstrong | A61F 5/445 |

FOREIGN PATENT DOCUMENTS

| | | | |
|---|---|---|---|
| WO | 2014177723 | A1 | 11/2014 |
| WO | 2016019963 | A2 | 2/2016 |
| WO | 2021243082 | A1 | 12/2021 |

OTHER PUBLICATIONS

International Search Report & Written Opinion for WO 2021/243082 A1, dated Nov. 4, 2021.
International Search Report & Written Opinion for corresponding WO 2023/069735 A1, dated Mar. 27, 2023.
Extended European Search Report for corresponding European Application No. 21813623, dated. Jun. 14, 2024.

* cited by examiner

ENDOLUMINAL STOMA DEVICE

CROSS REFERENCE TO RELATED APPLICATIONS

This application is a National Stage Filing of PCT Application No. PCT/US2021/034619 filed May 27, 2021, entitled "Endoluminal Stoma Device", which claims priority to U.S. provisional patent application 63/031,285 to Armstrong, entitled "Endoluminal Stoma Device," incorporated herein by reference.

BACKGROUND

Colostomy plates typically consist of a square adhesive plate usually made of corya gum which is placed on the skin of the patient. The colostomy or the ileostomy protrudes through a central hole through the center of the plate and the colostomy bag is detached to the plate using a clip-on plastic device similar to a Zip-Lock bag. Colostomy plates are difficult to attach and remain attached to the skin of the patient especially if the skin is moist or if the skin becomes infected or irritated from the spillage of the stool. At this point, adhesives or glues are used in an attempt to stick the plate to the skin. Frequently, the plates fall off or the bag falls off and stool leaks onto the abdominal wall causing inconvenience and distress.

SUMMARY OF INVENTION

The current device avoids the need for colostomy plates, glues and adhesives. A self-retaining endo-luminal colostomy device is provided which avoids the traditional stoma plates and adhesives. The device incorporates a flexible or semi-rigid plastic sleeve which is generally cylindrical in shape. A ring, which can be made of plastic or polymer or other springy material, is located at each end of a sleeve. The inner ring, which is generally deformable with return to or close to its original shape upon deformation and release, is inserted into the lumen of the stoma using an introducer or flexible endoscope. Once inserted the inner ring unfolds and adopts its original circular form. By gently pulling on the outer ring, the inner ring is then pulled to the sub-fascial space the narrowest part of the stoma, where it becomes lodged. The outer ring can then be secured around the outer tip of the stoma to secure the channel through the device for ultimate collection of waste, In some embodiments, the outer ring is rolled over upon itself which shortens the plastic sleeve while securing the device around the stoma. The outer ring protects the stoma and forms a stable base to attach stoma devices such as colostomy bags or occlusive devices. The cylindrical sleeve, the inner ring and the outer ring, therefore create a self-retaining device to attach stoma bags, occlusive plates, voiding tubes, or other suitable structures. This design can avoid the use of plates, adhesives, or the like, and therefore avoids inflammation and/or ulceration of the peri-stomal skin.

The two rings may be equal or unequal in size and/or shape. There may also be a plurality of "inner rings", to improve traction of the device within the bowel lumen. The inner ring may be the same diameter, or slightly larger diameter than the inner lumen of the small or the large bowel, so enabling it to become lodged in the sub-fascial space. The diameter of the outer ring may be slightly larger than the diameter of a conventional stoma, so therefore sized to provide for covering the external stoma. The sleeve membrane or a portion thereof may be fenestrated or contain perforations to allow mucous secretions into the lumen of the bowel.

In a first aspect, the invention pertains to an endoluminal stoma channel comprising a resilient deformable inner ring, an outer ring, a flexible polymer sleeve connected to the inner ring and the outer ring to form a flow channel and comprising a biocompatible polymer, and a tether comprising a cord and a knob. In general, the cord is attached to the inner ring, and the knob has a position such that the cord can extend along the sleeve, in the interior or exterior of the sleeve, past the outer ring with the outer ring pulled away from the inner ring such that the sleeve is taut. The words sleeve and membrane are used interchangeably herein for convenience.

In a further aspect, the invention pertains to a method for controlling release from a stoma through an endoluminal stoma channel comprising a resilient deformable inner ring, an outer ring, and a flexible polymer sleeve connected to the inner ring and the outer ring to form a flow channel and comprising a biocompatible polymer. The method comprises engaging a cover with a clamp onto the outer ring of the endoluminal stoma channel, wherein the inner ring is located within the patient with the flexible polymer sleeve extending outward from the stoma with the outer ring positioned outside the stoma, wherein the cover provides closure of the stoma or a controlled pathway for releases from the stoma.

In another aspect, the invention pertains to a stoma discharge control system comprising:

- an endoluminal stoma channel comprising a resilient deformable inner ring, an outer ring, and a flexible polymer sleeve comprising a biocompatible polymer and connecting the inner ring and the outer ring; and
- a cover comprising a clamp or seal element configured to engage the outer ring in a sealed engagement, wherein the cover provides an opening, a connector element, a closed surface or a combination thereof.

OVERVIEW OF THE DRAWINGS (FIG. 1)

Figure 1:
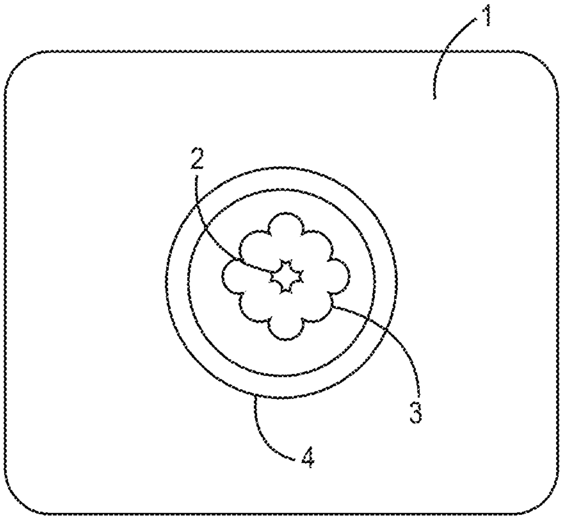
FIG. 1 is a front view of a conventional ostomy place positioned around as stoma.

A prior art colostomy plate 1 with the lumen of the colon 2 which is located in a hole 3 located in the middle of the colostomy plates. Around the periphery of the hole, a plastic ring 4 is located where the colostomy bag 5 may be detachably attached to the stoma plate and replaced for emptying and cleaning, etc.

(FIG. 2)

A transverse view of a colostomy showing the colostomy plates 3 which is adherent to the skin of the abdominal wall 6. The bowel [colon or ileum] is tunneled 7) through the abdominal wall 8 to create a colostomy or ileostomy 9. The point where the colostomy enters the abdominal wall "tunnel" 9 is referred to as the sub-fascial space 10 and is typically the tightest and most narrowed part of the stoma.

(FIG. 3)

The device is a flexible, elastic generally cylindrical sleeve 11 with two rings attached made of flexible, or malleable or semi-rigid plastic or polymer. An inner ring 12 is located within the lumen of the stoma and lodges in the sub-fascial space. The outer ring 13 is rolled upon itself so shortening the length of the sleeve membrane 11. The outer ring is prevented from "unrolling" by a "split ring" configuration having a non-circular cross-section area similar to a figure of 8. The membrane may be transparent or opaque, non-elastic or elastic.

(FIG. 4)

The cylindrical sleeve 11 is made shorter by rolling the outer ring 13 upon itself. The diameter of the outer ring is sufficient to cover the external ileostomy or colostomy and facilitates the placement colostomy bags, occlusive plates and irrigation systems.

(FIG. 5A)

Transverse section of a stoma with the device located in the lumen. The bowel 14 is tunneled through the abdominal wall 15 to make an external stoma which protrudes above the skin level 16. The inner ring of the device 17 is located within the lumen of the colon and is gently pulled distally until it lodges in the sub-fascial space 19. The outer ring 20, is rolled over upon itself so shortening the length of the sleeve or membrane 21, which keeps the inner ring secured in the sub-fascial space 19. The outer ring 20 also covers the external stoma 16 to protect it, and to facilitate placement of the bags or other structures described herein to the outer ring.

(FIG. 5B)

In obese individuals with thick abdominal walls 15, or when the sub-fascial space 19 is abnormally wide, as in para-stomal hernias, the inner ring 17 may deploy at a narrowing of the colon 18 closer to the surface in the lumen than the sub-fascial space 19, anywhere within the boundaries of the abdominal wall 15. The endo-luminal device therefore creates a tunnel 22 through the abdominal wall and provides a stable platform to place bags or other structures.

(FIG. 6A)

The device may be generally cylindrical in form or alternatively conical. The inner ring 23 may be smaller than the outer ring 24, so creating an inverted conical shape 25. The smaller ring located within the lumen of the bowel on the outer ring is located on the abdominal wall of the patient.

(FIG. 6B)

In an alternative scenario, the inner ring may be larger 26 than the outer ring 27. This then forms a cone shape 28.

(FIG. 6C)

In an alternative embodiment, the membrane 29, may be tapering at its center 30 with a thinner central waist compared to the inner ring 31 and the outer ring 32.

(FIG. 7)

The inner ring is delivered into the lumen of the bowel by folding the inner ring 32 into an elliptical form, or twisting into a figure of 8 and again upon itself to form a circular form 32. The inner ring is then inserted into the lumen of the bowel. The membrane 33 and the outer ring 34 remain above the abdominal wall.

(FIG. 8A)

A delivering device 35 may comprise a generally tubular device, which may be non-flexible, or flexible. Alternatively, a flexible endoscope or the like may be used to insert the inner ring. The inner ring is folded into a figure of 8 and compressed 36, and is inserted into the distal opening of the introducer 35, or around the end of the introducer. The outer ring and membrane 37 are located around the outside of the circumference of the delivery device or endoscope 35. Furthermore, forceps or the like can grip the ring in a reduced profile for insertion into the stoma. The delivery device or endoscope is then inserted into the colostomy and proximal to the sub-fascial space. The inner ring 36 is then gently pushed from the lumen of the delivery device or endoscope for instance using a pusher, or rod, the ring unfolds to form a circular form, and delivery device is removed.

(FIG. 8B)

The inner ring can be provided as an inflatable ring 101 that can be inserted in an uninflated state where the ring is manipulatable. As in FIG. 8A, the outer ring and membrane 37 are located around the outside of the circumference of the delivery device, and the delivery device 35 can be used for inserting the inner ring into the colostomy and proximal to the sub-fascial space. A fluid conduit 102 extends form inflatable inner ring 101 to a position that will be located external to the patient. Fluid conduit 102 can be connected to a small balloon 103 and terminates at a valve 104, such as a Tuohy-Borst valved adapter, that provides for the attachment of a syringe or the like to inflate or deflate the ring through changing the pressure in the enclosed system extending from inner ring 101 to the valve. The small balloon 103 can provide an indication of the pressure within the enclosed system and thereby the state of inflation of inflatable ring 101. Outer ring 37 can be made inflatable also if desired using a similar valved structure.

(FIG. 9)

Figure 10:
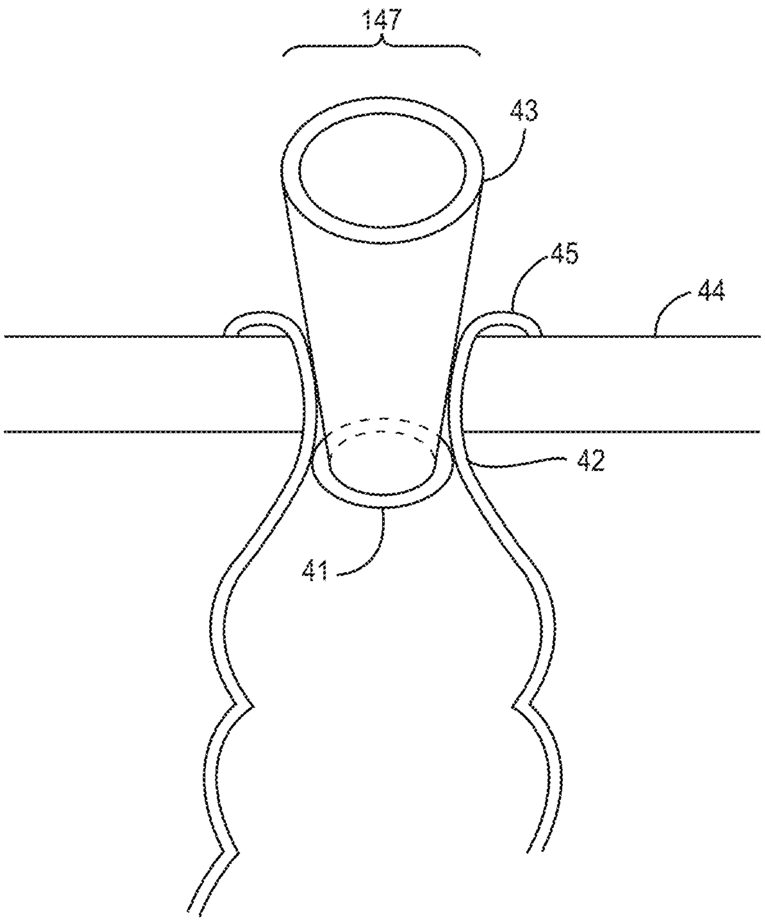
FIG. 10 is a schematic sectional view showing an endoluminal stoma channel in a deployed position within a stoma.

The inner ring of the device may be introduced into the bowel by applying traction on the inner ring so deforming it into an oval shape. This may be performed by a simple rod shaped device, with a "V" shaped tip 38, passed into the outer ring and sleeve 37 or by applying traction to the pull-string 40 of the inner ring 39, for instance by using biopsy forceps of a conventional flexible endoscope inserted into the outer ring and sleeve 37. The inner ring 39 or rings are placed under traction using the V tipped device 38 or by traction on the pull-string 40 which deforms the inner ring 39 or rings into an elliptical shape, which facilitates their placement into the stoma without trauma or pressure, and then released. The biopsy forceps of a conventional endoscope, passed through the outer ring and sleeve 37 may be used to grasp the "pull-string" 40 of the inner ring, and pulls the inner ring into the sub-fascial-space (FIG. 10)

The inner ring 41 is deployed into the lumen of the bowel and it resumes its previous circular form. It is then gently pulled up into the sub-fascial space 42 where it lodges. Having removed the introducer, the outer ring 43 is then rolled upon itself until it reaches the skin of the anterior abdominal wall 44 and covers or protects the external stoma 45.

(FIG. 11)

A plurality of inner rings 46, of equal diameter, are configured in parallel along the sleeve 47, in order to increase traction within the lumen of the bowel 47, do diminish the chances of perforation of the bowel wall.

(FIG. 12)

In a further configuration, the diameter of the inner rings 49 may decrease progressively toward the sub-fascial space. In this configuration peristalsis of the bowel 50 tends to compress the rings together, forming a pyramidal or conical form, so maintaining the inner rings with more stability within the lumen.

(FIG. 13)

An embodiment of an endoluminal stoma channel comprises an outer ring 110, inner ring 111, membrane 112 connecting outer rig 110 and inner ring 111. Tether 113 is connected to inner ring 111 in a configuration to run along the outside of membrane 112. Tether 113 has a knob 114 at is end.

(FIG. 14)

Alternative embodiment of an endoluminal stoma channel comprises a tether 113 attached to inner ring 11 in a configuration to extend within membrane 112 and pass through outer ring 110. This embodiment also has a knob 114 at the end of tether 113.

(FIG. 15)

Figure 13:
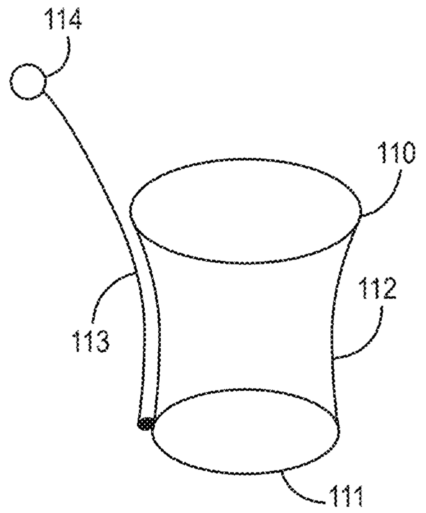
FIG. 13 is a perspective view of an endoluminal stoma channel having a tether connected to the inner ring and configured exterior to the sleeve.
Figure 15:
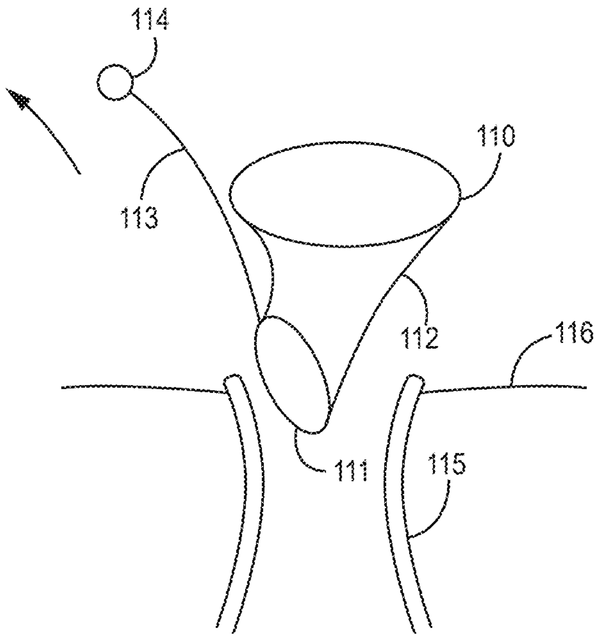
FIG. 15 is a schematic sectional view depicting the removal of the endoluminal stoma channel of FIG. 13 through pulling on the tether/pull-string.

The removal of the endoluminal stoma channel of FIG. 13 can be effectuated as shown in FIG. 15. Pulling on tether or pull string 113 distorts inner ring 111 such that the device can be removed out from the patient's stoma.

(FIG. 16)

Figure 14:
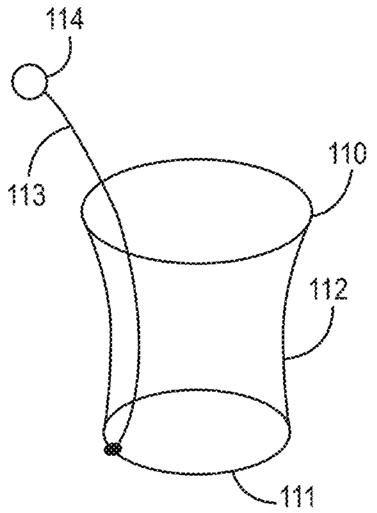
FIG. 14 is a perspective view of an endoluminal stoma channel having a tether connected to the inner ring and configured interior to the sleeve and extending through the outer ring.
Figure 16:
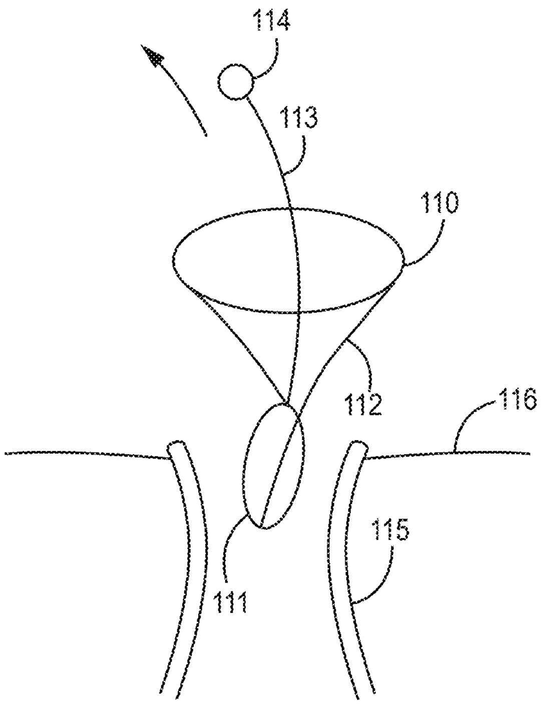
FIG. 16 is a schematic sectional view depicting the removal of the endoluminal stoma channel of FIG. 14 through pulling on the tether/pull-string.

The removal of the endoluminal stoma channel of FIG. 14 can be effectuated as shown in FIG. 16. Pulling on tether or pull string 113 distorts inner ring 111 such that the device can be removed out from the patient's stoma.

(FIG. 17)

An embodiment of an attachable bag 51 is shown separate from the colostomy attachment device, endoluminual stoma channel 52. Bag 51 is designed for attachment to the outer ring. Bag 51 has a fastener 52 that can comprise a clamp or seal element with a releasable lever to attach and remove the bag or a snap-type design or the like similar to conventional colostomy bags. Bag 51 can have a closable drain 54 with a hook and loop closure 55 or a clamp closure or the like, although in other embodiments the bag is sealed on its end for disposal and replacement of the bag rather than drainage.

Figure 17:
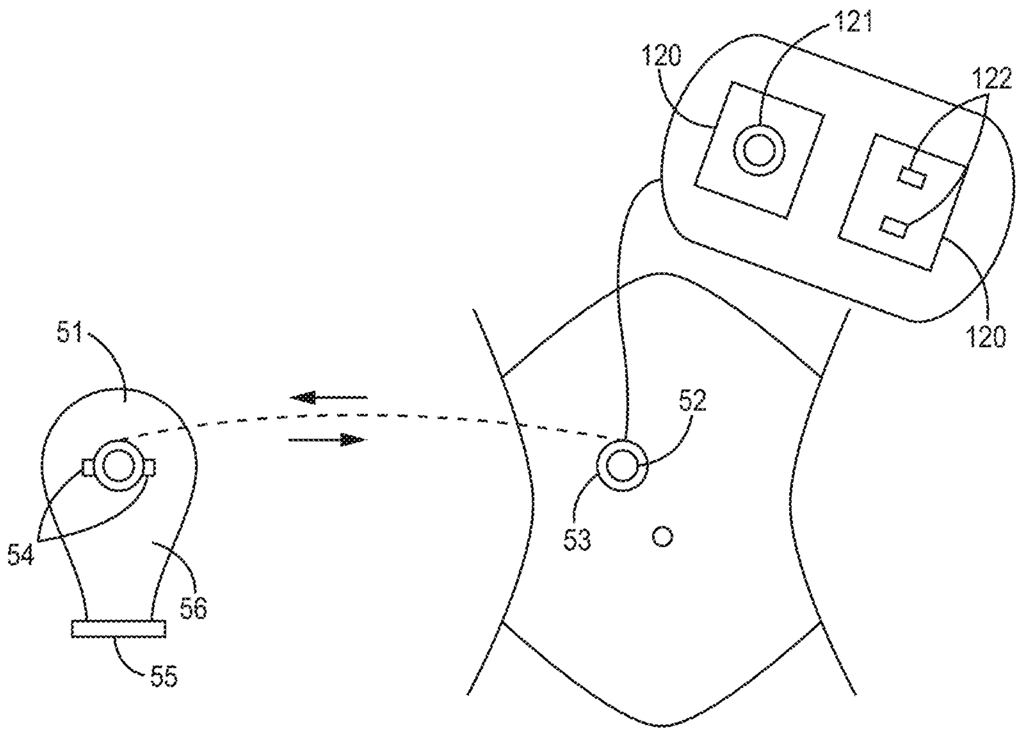
FIG. 17 is a front view of an abdomen with an endoluminal stoma channel deployed in a stoma and an adjacent collection bag with a connector element suitable to engage the outer ring of the endoluminal stoma channel, with a figure insert depicting an optional place to engage the outer ring to provide a connection element suitable to engage the bag.

(FIG. 17 Inserts)

An embodiment adapted from the device of FIG. 17 is shown in the inserts of FIG. 17. The endoluminal stoma channel is shown with the outer ring replaced or supplemented with a wafer-type structure 120. The inner ring and sleeve can correspond with any of the embodiments described herein. Wafer-type structure 120 can be permanently attached or releasably attached to an outer ring using similar attachment as described in the context of FIG. 17. Wafer-type structure 120 further comprises a fastener 121 for the attachment of a bag. Fastener 121 can be any reasonable structure such as a snap structure or the like.

(FIG. 18A)

In a further embodiment, an inflatable balloon is 59 provided, attached to a fluid conduit 60, which is inflated in a similar manner as the balloon on a Foley catheter. The deflated balloon is inserted through the lumen 61 of the deployed device 62 and positioned proximal to the inner ring 63 of the deployed device. The balloon 59 is then inflated with fluid via the fluid conduit 60. The Fluid conduit has a valve 65 such as a luer lock valve which maintains pressure within the balloon and prevents leakage from the balloon 59.

(FIG. 18B)

Figure 19A:
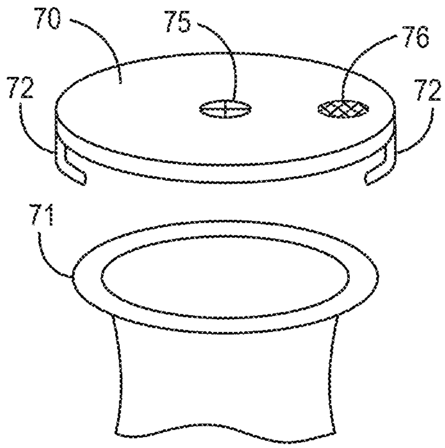
FIG. 19A is a fragmentary, perspective view of an outer ring and portion of sleeve of an endoluminal stoma channel with a snap engaging cap positioned adjacent the outer ring, in which the cap is shown with optional valve and optional vent.
Figure 19B:
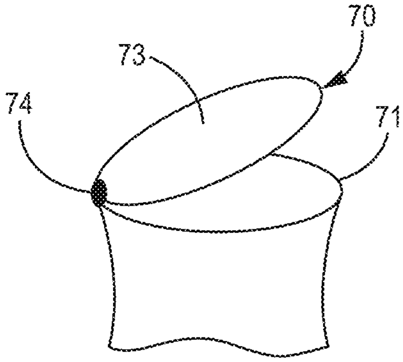
FIG. 19B is a fragmentary, perspective view of an outer ring and portion of sleeve of an endoluminal stoma channel with a hinged cap connected to the outer ring.

The inflated balloon 59 is pulled gently toward the inner ring 63 of the device and forms a seal between the inflated balloon and the inner ring of the device, similar to a "Ball valve" device. The inflated balloon prevents stool, liquid and gas from exiting through the device and creates a stable mechanical seal between the balloon and the inner ring. The inflatable fluid conduit may be secured at the outer ring 66 or the plate attached to the outer ring by a slot or key-hole type configuration 67 which secures the balloon at the inner ring 63 and maintains the seal between the balloon and the inner ring (FIG. 19A)

A cap 70 with clasps 72 is shown adjacent an outer ring 71 configures for connection of the cap onto the outer ring. Optional valve 75 and optional vent 76 are depicted on the surface of cap 70.

(FIG. 19B)

An alternative embodiment of a cap 70 has a hinge 74 connecting cap 70 to outer ring 71.

(FIG. 20)

Figure 21:
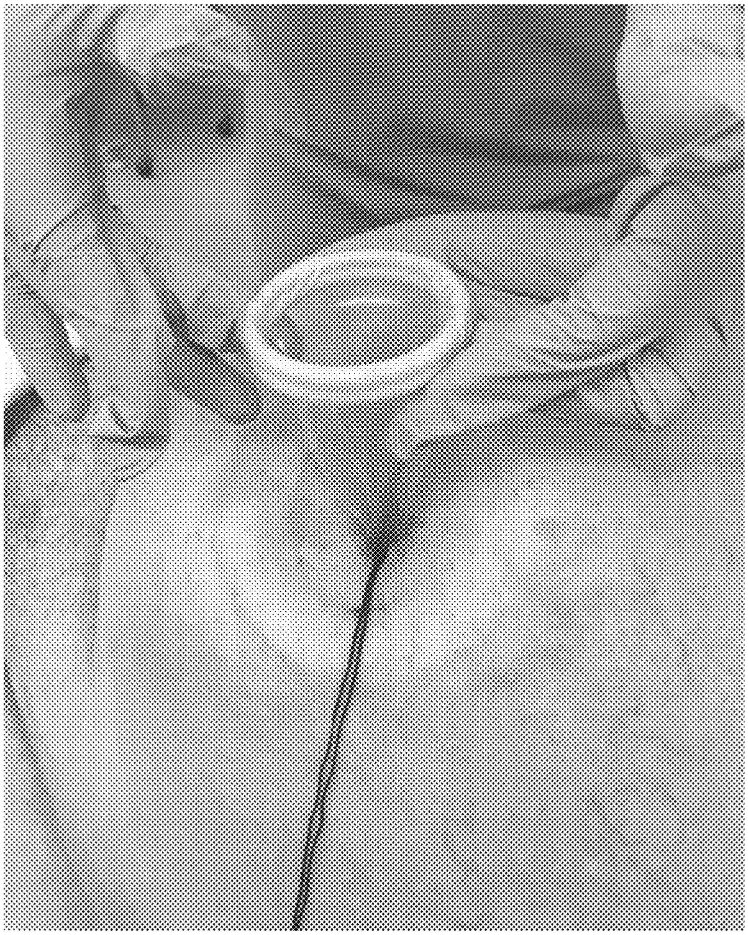
FIG. 21 is a photograph of the patient's stoma with an endoluminal stoma channel partially inserted.

A 57 year old morbidly obese male undergoes a Hartmanns resection for perforated diverticulitis. Because of his obesity, and a 5 in deep abdominal wall, the end of the colostomy underwent ischemic necrosis, leaving a pencil thin "blow-hole+fistula (FIG. 21)

Figure 22:
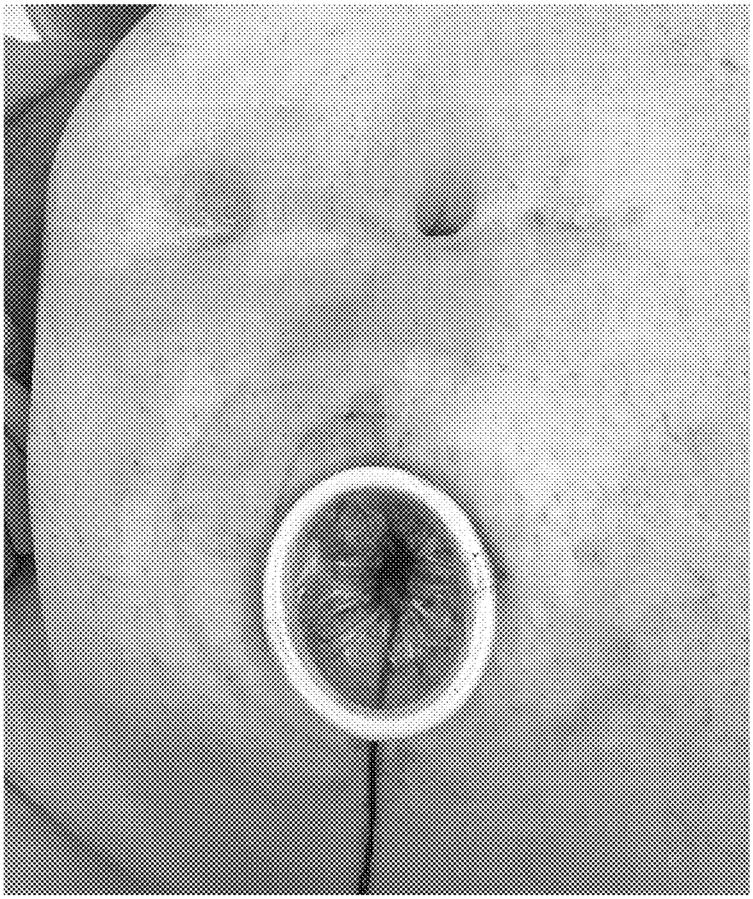
FIG. 22 is a photograph of the patient's stoma with an endoluminal stoma channel inserted into the stoma and an outer ring folded over the stoma to cover the stoma.

The device was inserted into the "blow-hole" colostomy forming a stable platform for placement of a colostomy bag (FIG. 22)

The device was stable and remained in place and even applying significant traction to the device. The patient underwent a successful bowel prep to clean out the colon, and had surgery to reverse the colostomy.

DETAILED DESCRIPTION OF THE INVENTION

The devices described herein provide for secure interface with a stoma formed with colon or ilium (small bowel) by placement of a sleeve extending from the stoma and secured with a ring anchored within the patient. The sleeve can be conveniently placed within the patent to provide a way to control output from the stoma without gluing something to the patient's skin. The ostomy device can be referred to an endoluminal stoma channel, and these terms are used interchangeably herein for convenience. Various covers are described to secure onto an outer ring to provide desired control and controlled access. The endoluminal stoma channel and a cover as well as other possible components can be referred to as a stoma discharge control system, although the components can be referred to without specific reference to the system. The rings generally can have a circular shape in the plane of the ring, but other shapes can be effective too, especially for the outer ring. For example, the inner ring can have a minor oval shape. While an outer ring with a circular shape can fit snugly over the stoma, other shapes such as a square can also fit over the stoma and may provide different attachment modalities for covers and the like.

In contrast with the stoma anchored devices described herein, referring to FIG. 1 a typical colostomy device consists of an adhesive plate 1 with central hole 2 and through which a colostomy or ileostomy protrudes 3. A clip or seal attachment 4 around the circumference of the hole allows detachment of colostomy bags and the stool empties into the bag. The bag is emptied and cleaned from time to time or replaced.

Figure 2:
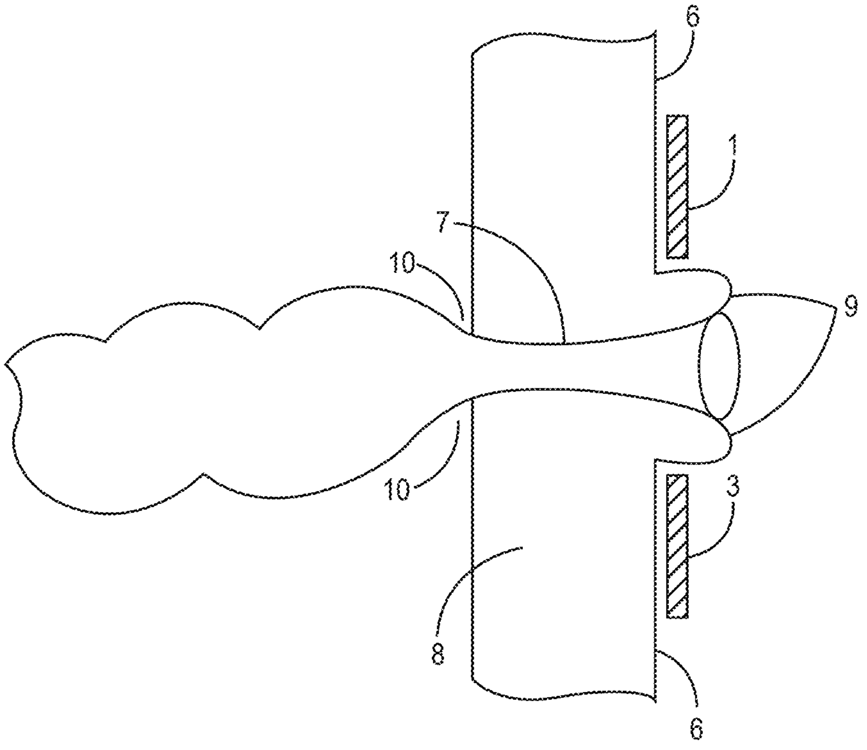
FIG. 2 is a schematic sectional view depicting a section of bowel passing through an abdominal wall to form a stoma that has a conventional stoma plate attached around the stoma.

Referring to FIG. 2, the depiction illustrates a cross-section of a conventional colostomy with a prior art colostomy device of FIG. 1 secured to the patient. The colostomy plate 1 adheres to the skin of the abdominal wall 6. The colostomy bag is attached to the plate using a plastic snap-on or clip-on mechanism similar to a Zip-Lock bag, as known in the art. The bowel itself 7 is tunneled through the anterior abdominal wall 8 and forms an external colostomy or ileostomy depending on whether the colon [colostomy] or ileum [ileostomy] 9 is used. The narrowest part of the stoma is at the sub-fascial space 10, where the bowel enters the abdominal wall 6. Stomas are used after resection of the bowel or when re-anastomosis of the bowel is not feasible, for instance after Abdomino-perineal resection for the rectum for cancer.

Figure 3:
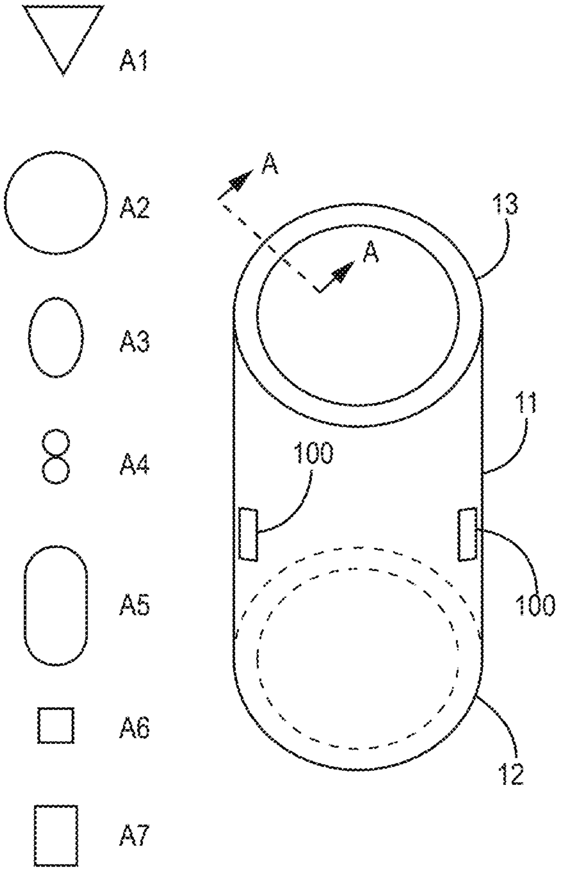
FIG. 3 is a perspective view of an embodiment of an endoluminal stoma channel, with various cross sectional shapes of the rings shown in the A1 to A7 sectional views taken along line A-A.

Referring to FIG. 3, the current device comprises a generally cylindrical plastic membrane 11 with an inner ring 12 and outer ring 13 attached to the membrane, such as through adhesive bonding, heat bonding, or other suitable procedure. The plastic membrane may be fenestrated or contain perforations 100 to allow mucous secretions into the lumen of the bowel. The rings can be made of either flexible, soft or semi-rigid polymer or plastic, spring metal (e.g., Nitinol) or combinations thereof, and the inner ring and the outer ring can be made from the same or different material(s). The inner ring and/or the outer ring can be inflatable to facilitate placement and securing of the ring, and an appropriate tube with a suitable valve can be located to be accessible outside of the patient to allow for inflating and deflating the ring. Catheter balloons, balloon lumen and appropriate valves are known in the art, such as in association with Foley catheters. In some embodiments, the outer ring has a non-circular cross section and can be rolled upon itself to shorten the sleeve membrane. Representative cross sectional shapes for either inner ring 12 or inner ring 13 are shown in FIG. 3A, A1 through A7; triangular, circular, oval, FIG. 8, elongated curved, square or rectangular. The ring can be prevented from "unrolling" by a "split ring" configuration having a cross-section area similar to a figure of 8, similar to Figure A4. Alternatively, the cross sectional profile may be ovoid, triangular, or polyhedral. This facilitates rolling the outer ring over and over itself, toward the inner ring and thereby making the length of the central membrane 11 shorter. The membrane may be transparent, translucent, or opaque. The membrane may be non-elastic or elastic, although the membrane is generally flexible and tear resistant. Elastic or "stretchable" membranes facilitate deployment and securing the device. Various biocompatible polymers are known in the art, such as latex, polyesters, polyamines, vinyl polymers, and the like. The membranes may be fenestrated or contain perforations or holes to allow mucous to enter the lumen of the bowel. The length of the endo-luminal device between planes of the rings with the inner and outer rings gently pulled away from each other may be 0.5 to 20 cm, in some embodiments 3-18 cm and in further embodiments 5-16 cm total length. The cross-sectional diameter of the individual inner and outer rings may be 0.05-2 cm, in other embodiments 0.1-1 cm and in further embodiments 0.25-0.5 cm. A person of ordinary skill in the art will recognize that additional ranges of dimensions within the explicit ranges above are contemplated and are in the present disclosure.

Figure 4:
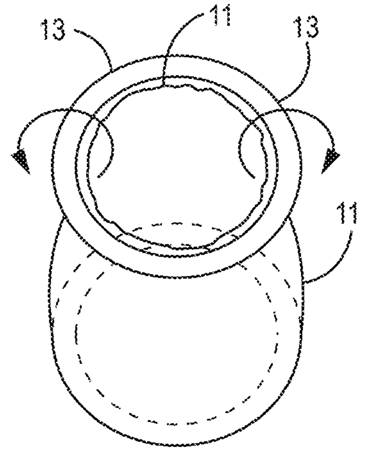
FIG. 4 is a perspective view of an endoluminal stoma channel with the outer ring rolled over to shorten the sleeve.

Referring to FIG. 4, the outer “split ring” 13 is rolled upon itself either inwardly or outwardly thus rolling up the central membrane 11 around the circumference of the outer ring 13. The central membrane 11 is thereby shortened. In further alternative embodiments, sets of devices can be sold with various lengths of the cylindrical membranes so that the size can be selected for use with a particular patent. In additional or alternative embodiments, devices can be sold so that the length of the membrane can be adjusted and clipped at a certain length, with or without rolling the outer ring, to achieve a selected membrane length for the patient prior to deployment. In an alternative embodiment, the outer ring may be detachably attachable to the cylindrical membrane, so the length of the cylindrical membrane may be cut to length, according to the body habitus of the patient (long length of cylindrical sleeve needed for obese patients; shorter lengths for thinner patients), and then clipped to the ring. Similar, devices (Alexis retractor, Applied Medical CA) are used to provide exposure for incisions in the abdomen or during cesarean section, but these devices are larger and designed for different techniques for delivery and removal.

Figure 5A:
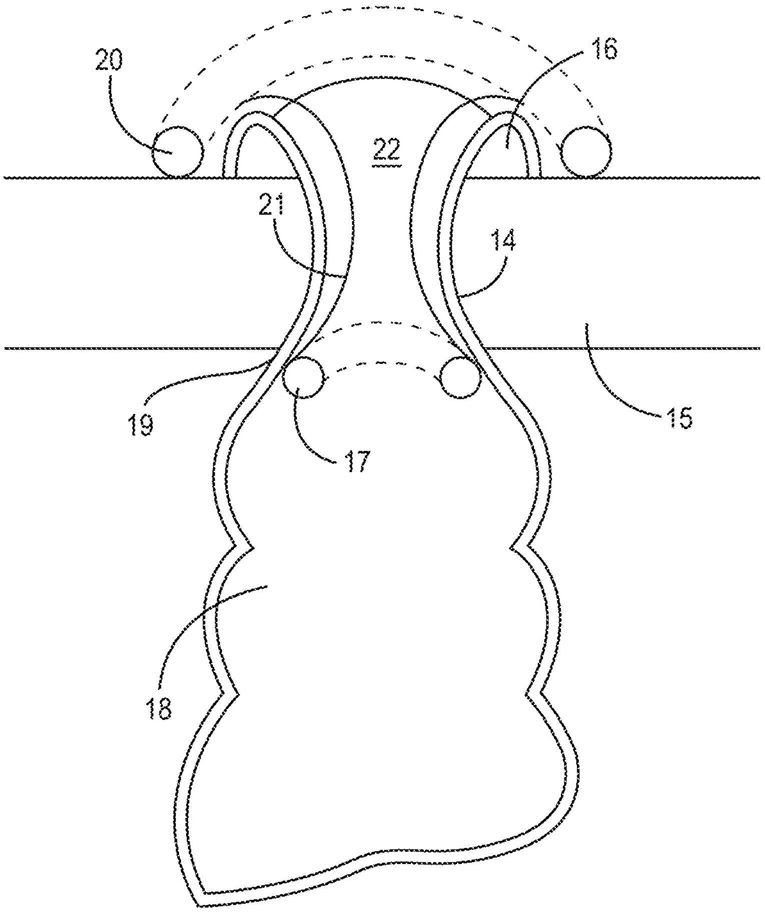
FIG. 5A is a schematic sectional side view of a bowel connecting to a stoma passing through the abdominal wall with an endoluminal stoma channel positioned within the stoma.

Referring to FIG. 5A this illustrates a cross-section of a colostomy or ileostomy of the device in place. The colon 14 or ileostomy is tunneled through the anterior abdominal wall 15 and an external stoma 16 is created by everting the cut edge of the bowel to form a spout. This facilitates placing a colostomy plate and avoids ulceration or digestion of the skin around the stoma. The inner ring of the device 17 has a diameter either equal to, or slightly larger than the diameter of the inner lumen of the small bowel or colon of a human. Generally, this diameter is 0.1-10 cm, in same embodiments 0.5-7 cm, in further embodiments 1-6 cm diameter. The diameter of the bowel may vary widely in certain pathological conditions, and various sizes of device can be available, depending on the individual stoma (for instance, small; medium and large). Upon delivery onto the stoma, the inner ring 17 can be pulled gently toward the sub-fascial space 19 by applying gentle traction to the outer ring. The sub-fascial space 19 is typically the narrowest part of the stoma, since the bowel is constricted as it enters the tunnel through the abdominal wall 15, and provides a ledge where the inner ring 17 lodges.

The outer ring 20 can be rolled upon itself and the length of the sleeve membrane 21 is thereby shortened. The outer ring 20 may be equal diameter or larger than the inner ring 17. The diameter of the outer ring is generally 1-12 cm, in some embodiments 2-10 cm in diameter, and in further embodiments 3-8 cm in diameter. A person of ordinary skill in the art will recognize that additional ranges of inner ring diameters and outer ring diameters within the explicit ranges above are contemplated and are within the present disclosure. As the outer ring 20 can be rolled upon itself it deploys circumferentially around the outer stoma 16 so protecting it from drying or injury. The outer ring 20 then creates a stable platform wearing a stoma bag or occluding plate may be detachably attached using a clip mechanism or flip-on mechanism. The need for plates, glues and adhesives is therefore avoided, and erosion breakdown or ulceration of the skin which is often seen in current colostomies can be avoided.

Figure 5B:
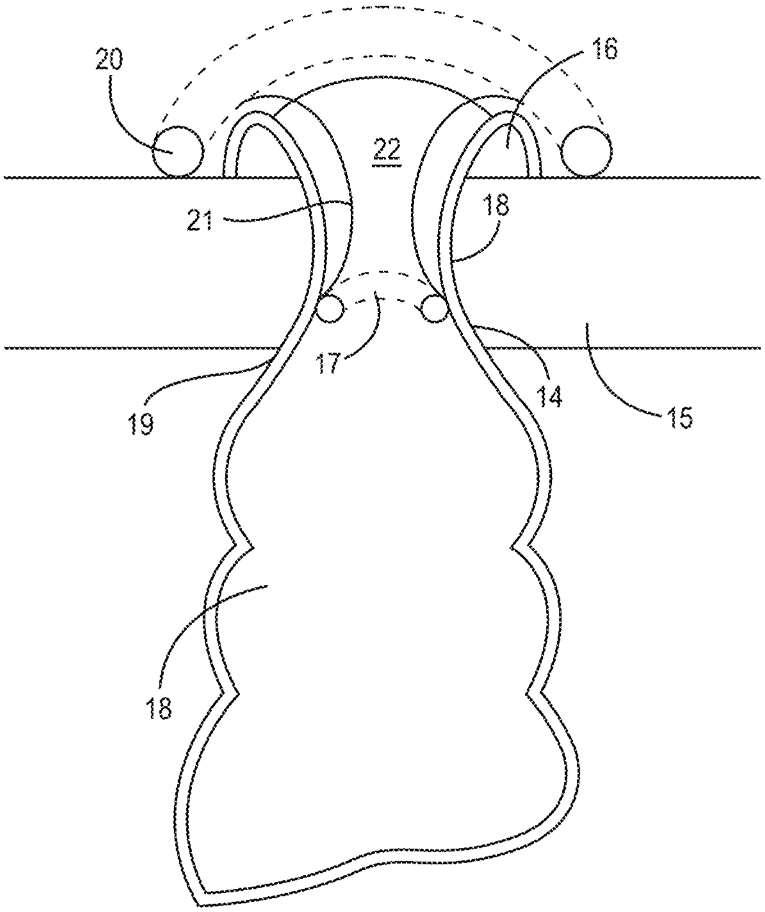
FIG. 5B is a sectional side view of a embodiment where the inner ring of an endolumenal stoma channel secured at a position closer to the surface of the abdominal wall.

For a configuration with a ring deployment not as deep in the stoma, referring to FIG. 5 B, the inner ring 17 may be deployed at a site in the lumen closer to the surface than the sub-fascial space 19. This may occur in obese individuals with very deep abdominal walls 15, or in the presence of an abnormally enlarged sub-fascial space 19 as occurs in the presence of a para-stomal hernia. For instance, the inner ring 17 may deploy at a site or narrowing 18 within the boundaries of the abdominal wall 15, between the sub-fascial space 19 and the external stoma 16. In this scenario, the inner ring 17 lodges at the most narrow part of the lumen 18. In this scenario, radial traction from the inner ring 17 maintains the inner ring in place.

Figure 6A:
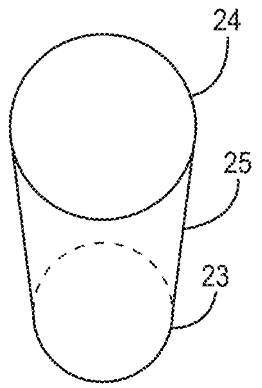
FIG. 6A is a perspective view of an endoluminal stoma channel with an outer ring larger than the inner ring connected with a conical shaped sleeve.
Figure 6B:
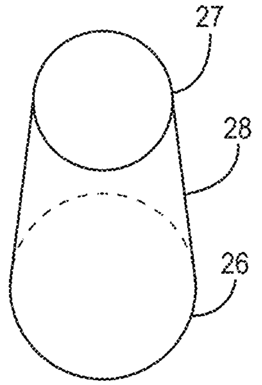
FIG. 6B is a perspective view of an endoluminal stoma channel with an outer ring smaller than the inner ring connected with a conical shaped sleeve.
Figure 6C:
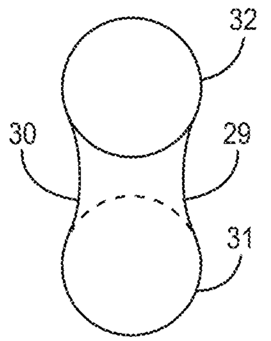
FIG. 6C is a perspective view of an endoluminal stoma channel with an outer ring roughly the same size as the inner ring connected with a sleeve shaped with a central taper.

Referring to a representative embodiment in FIG. 6A, the inner ring 23 may be smaller than the outer ring 24, as in an inverted cone 25 configuration. This allows for the inner ring to be located within the lumen of the small bowel or large bowel and the outer ring may be large enough to cover the external aspect of the colostomy or ileostomy. FIG. 6B illustrates an embodiment with an upright cone where the inner ring 26 is larger than the outer ring 27 and the central membrane 29 is in the form of an upright cone. FIG. 6C, is another alternative configuration where the inner membrane 29 may be wasted or narrow 30 where the central portion of the membrane is narrower than the inner ring 31 or the outer ring 32.

Figure 7:
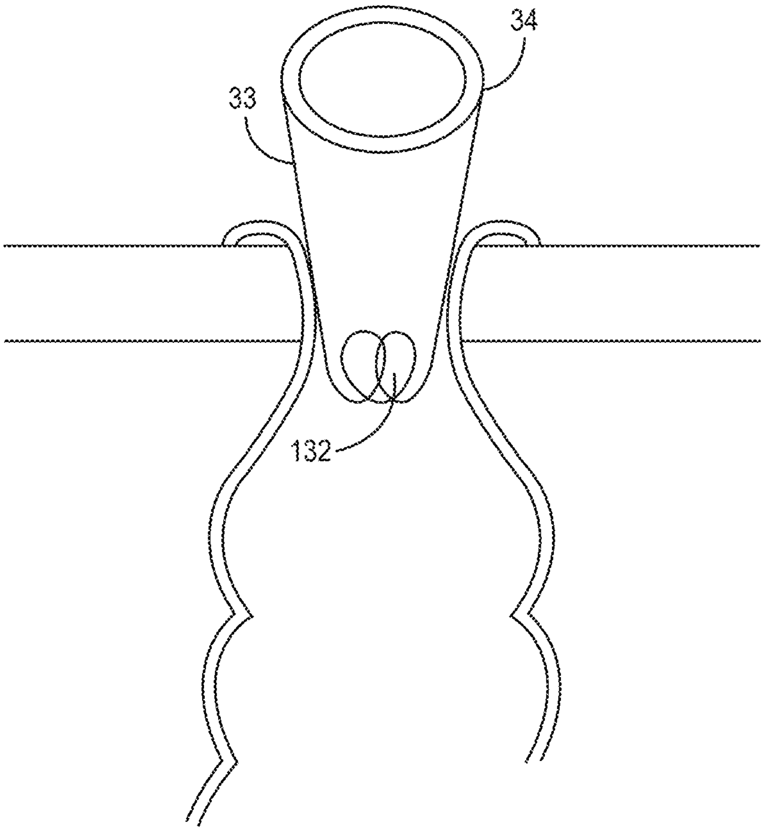
FIG. 7 is a schematic sectional view showing an endoluminal stoma channel with a compressed inner ring inserted into the stoma for placement of the device.

Referring to FIG. 7, the inner ring 32 is deployed into the lumen of the bowel by folding the semi-rigid or elastic inner ring into a figure of 8 and then folding it upon itself once again to form a circular configuration. This makes the diameter of the inner ring smaller and easier to introduce into the lumen of the bowel. The inner ring is then inserted into the lumen of the bowel, such as manually or with forceps, and the membrane 33 and the outer ring protrudes above the abdominal wall.

Figure 8A:
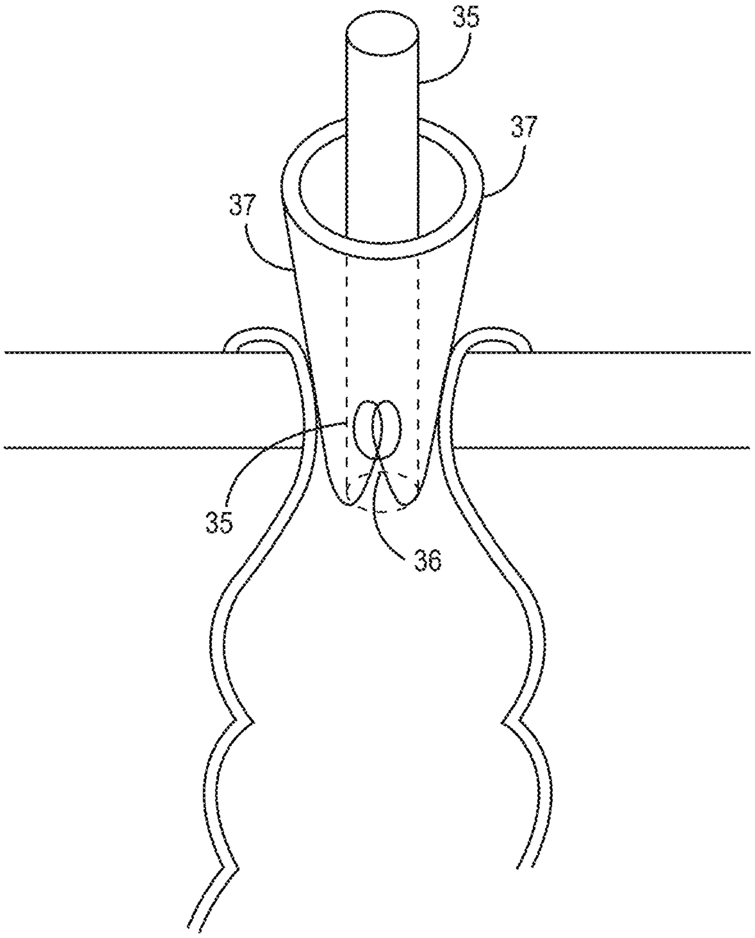
FIG. 8A is a schematic sectional view showing an endoluminal stoma channel with a compressed inner ring within an introducer lumen for facilitating placement of the device.

Referring to FIG. 8A a tubular introducer or endoscope 35 may be used to introduce the folded inner ring into the stoma. The introducer may be solid or tubular, and either non-flexible or flexible, with dimensions generally from 0.5-5 cm or in further embodiments 1-2 cm diameter can be inserted into the lumen of the colostomy or the ileostomy. A person of ordinary skill in the art will recognize that additional ranges of introducer diameters within the explicit ranges above are contemplated and are within the present disclosure. The inner ring is compressed into a suitable distorted form, and introduced into the lumen of the introducer. Alternatively, a conventional upper endoscope or flexible endoscope may be used to insert the device. In one embodiment, the inner ring is twisted into a figure of 8, then into a circular form and placed into or around the distal aspect of the introducer device or endoscope 35. The outer membrane and outer ring 37 are located around the circumference of the introducer or endoscope as it is inserted into the stoma. The introducer or endoscope 37 is inserted into the lumen of the colostomy or the ileostomy and the inner ring 36 is pushed from the introducer lumen, for instance using a simple pusher device. In the event a flexible endoscope is used, a flexible biopsy forceps can be inserted through the biopsy channel of the endoscope, and detachably attached to the “pull-string” mechanism of the inner ring. When the inner ring is sufficiently inserted into the lumen of the bowel, traction is applied to the biopsy forceps, which applies traction to the “pull string” device, which in turn deploys the inner ring. The “pull string” device is then released from the biopsy forceps, and the endoscope is withdrawn. The inner ring 36 resumes its original circular form, and is deployed proximal to the sub-fascial space and is pulled into the sub fascial space where it lodges.

Figure 8B:
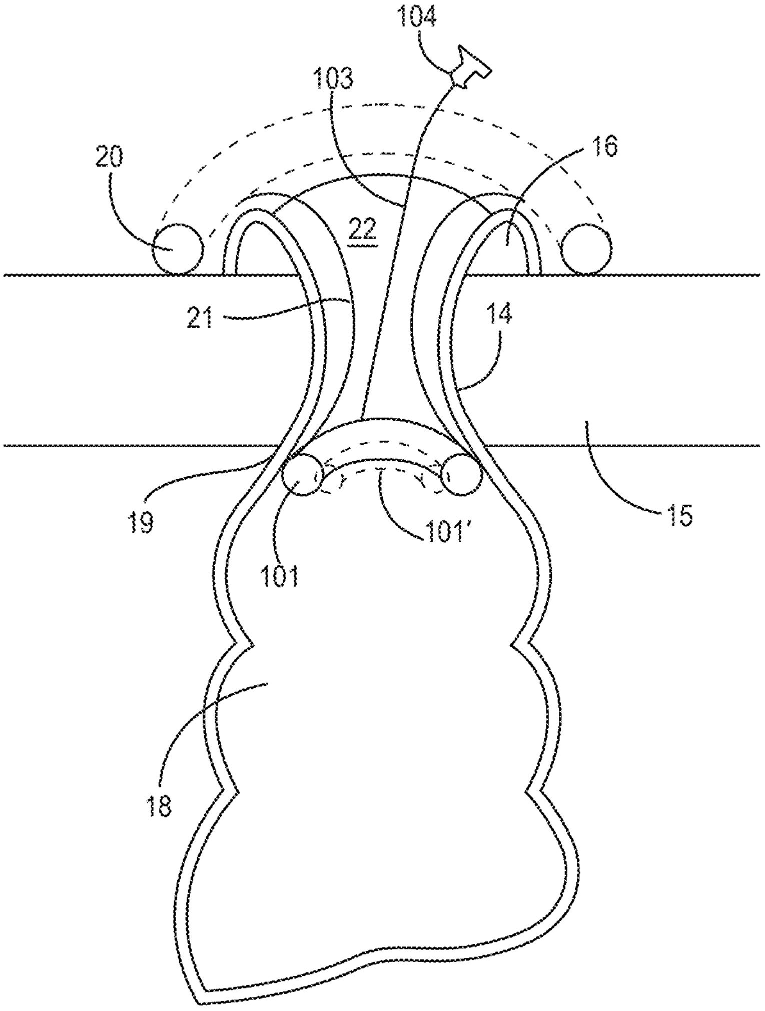
FIG. 8B is a schematic sectional view showing an endoluminal stoma channel with an inflated inner ring and with a deflated inner ring depicted in dashed lines.

An embodiment with an inflatable inner ring 101 (uninflated ring 101') is shown in FIG. 8B. In an uninflated stat of 101', the ring can be readily inserted into position. Once in position, the ring can be inflated and gently pulled into position. A balloon lumen 103 can be used to supply fluid, such as air or saline, to the balloon. A fitting, such as a Luer lock fitting, at the end of the balloon lumen can be used to connect to a syringe or other device to effectuate the fluid delivery or removal.

Figure 9:
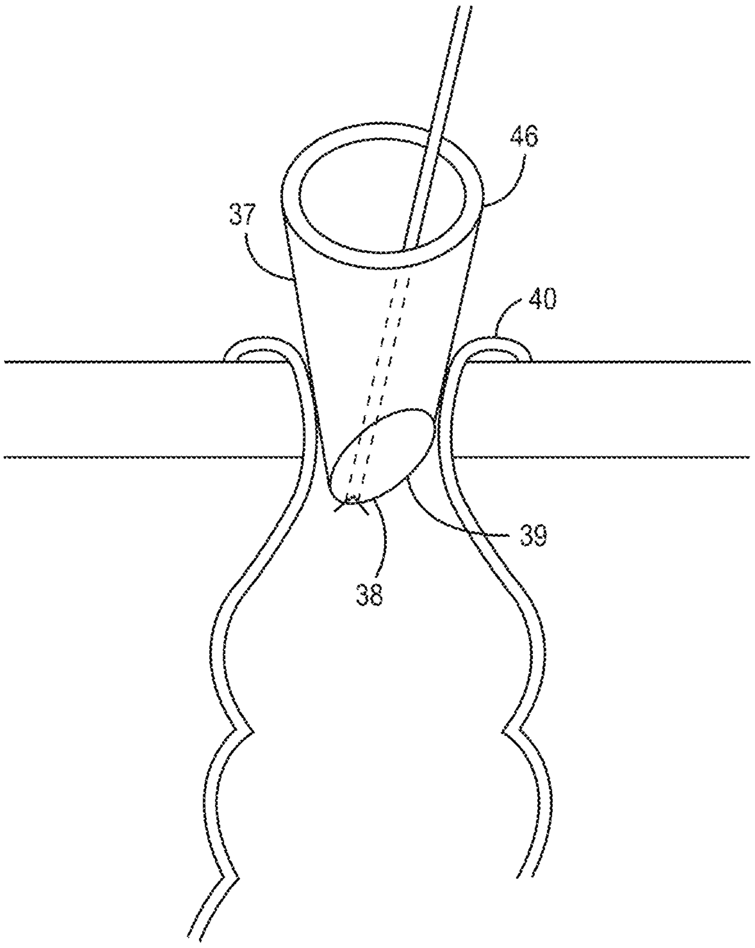
FIG. 9 is a schematic sectional view showing an endoluminal stoma channel with a distorted inner ring engaged with a delivery tool having a gripping element at its end.

Referring to FIG. 9, in an alternative configuration, the device may be introduced into the bowel by a simple rod shaped device, with a "V" shaped tip 38, inserted into the inner aspect of the sleeve 37, to engage the inner ring 39 or rings. The inner ring or rings are placed under traction using the V tipped device which deforms the inner ring or rings into an elliptical shape, which facilitates their placement into the stoma without trauma or pressure, and then released, by removing the inserting device. This allows the ring or rings to revert to its (their) original circular form, and become lodged in the sub-fascial space. In an alternative configuration, the inner ring 39 may be introduced by applying traction to pull string 40 of the inner ring 39 by a grasping device of a conventional upper endoscope or flexible sigmoidoscope, passed into the outer ring and sleeve 37. In this configuration, the pull string 40 attached to the inner ring 39 is grasped by a grasping device, such as a biopsy forceps, of a conventional endoscope. The biopsy forceps grasps the "pull string" 40, and "pulls' the inner ring 39 into the lumen of the stoma. Having reached the sub-fascial space, the "pull sting" 40 is released and the inner ring deploys in the lumen of the bowel, as described above. Similarly, the forceps can be used to directly hold the inner ring in a suitable configuration to enter the stoma.

Referring to FIG. 10, the inner ring 41 is inserted into the lumen of the bowel, and after it resumes its previous circular form, it can be gently pulled up into the subfascial space 42 where it lodges because of the more narrowed circumference of the bowel at that point. Having removed the introducer, the outer ring 43 can then be rolled upon itself or otherwise pulled down until it reaches the skin of the anterior abdominal wall 44 and covers or protects the external stoma 45. A colostomy bag may be detachably attached to the outer ring 46 and prevents the need for glue or adhesives. Alternatively, the occlusive plates or cover 47 may be detachably attached to the stoma and or the outer ring. Such occlusive plate/cover 47 can be flat or bowl shaped to cover the stoma and be secured to appropriate securing structure. Cover 47 can act as a seal element with respect to discharge from the stoma. Alternatively irrigating devices may be passed through the occluding plate to access the stoma or to extend into the stoma itself.

Figure 11:
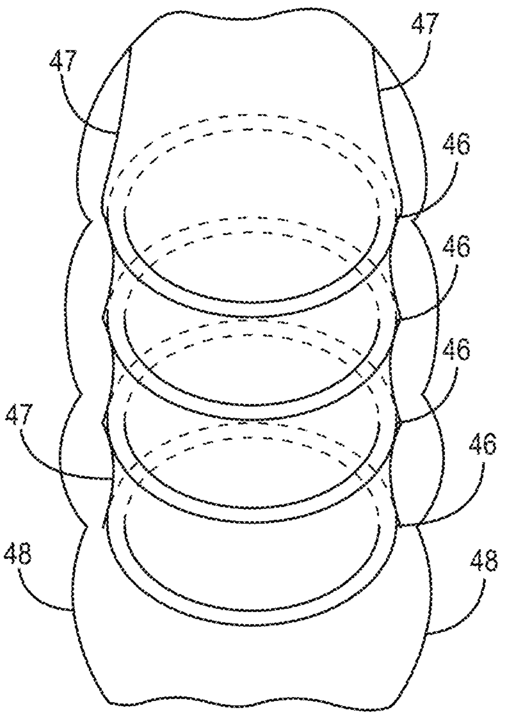
FIG. 11 a schematic sectional view showing an endoluminal stoma channel with a plurality of approximately equal sized inner rings.
Figure 12:
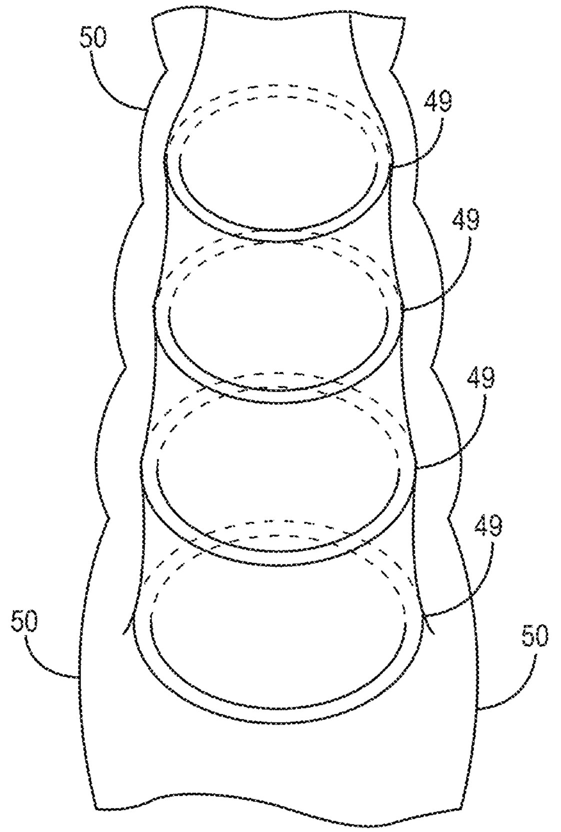
FIG. 12 is a schematic sectional view showing an endoluminal stoma channel with a plurality of inner rings with decreasing diameters for rings closer to the stoma opening outside of the patient.

Referring to FIG. 11, there may be a plurality of inner rings 46, to increase traction within the bowel 48, and reduce chances of pressure necrosis of the bowel 48. These rings may be equal to each other in diameter, in the manner of a concertina. The length of the membrane between the rings may be 0.1-10 cm, in some embodiments 0.2-5 cm, and in further embodiments 0.5-2 cm. Referring to FIG. 12, in a further configuration, the diameter of the inner rings 49 may decrease progressively toward the sub-fascial space 49. In this configuration peristalsis of the bowel 50 tends to compress the rings together, forming a pyramidal or conical form, so maintaining the inner rings with more stability within the lumen. The ranges of lengths between rings also apply to the embodiment of FIG. 12. The ranges of diameters of the inner rings described above apply equally for the embodiments of FIGS. 11 and 12. A person of ordinary skill in the art will recognize that additional ranges of length within the explicit ranges above are contemplated and are within the present disclosure.

In yet another configuration, the device may be release from the bowel by means of a "pull string", which is attached to the most proximal flexible ring of the device and deployed within the inner sleeve of the device. The "pull string" is of sufficient length that it protrudes from the ostomy, and is easily identifiable and accessible to the operator. Referring to FIG. 13, the device has an outer ring 110, inner ring 111 connected by membrane 112, and a tether comprising a cord or "pull-string" 113 is attached to inner ring 111. For convenience, the terms cord, and pull-string are used interchangeably herein, and tether can refer to the cord/pull-string or the cord/pull-string along with the knob, as will be clear in the context. The free end of cord 113 can have a knob 114 to allow for easier gripping of the tether. As shown in FIG. 13, cord 113 is attached to inner ring 111 in a configuration that positions cord 113 to have a natural position on the exterior of the device. Referring to FIG. 14, the device is similar to the device of FIG. 13, except that cord 113 is attached to inner ring 111 at a position that has a natural position with cord 113 along the interior of membrane 112. If cord 113 is long enough, in either embodiment of FIG. 13 or FIG. 14, tether 113 can be wrapped around inner ring 111 to place cord 113 in the interior of membrane 112 or along the outside of membrane 112. In general, cord 113 can be at least 2 cm longer than membrane 112 to allow for use of the tether, in further embodiments at least about 5 cm longer, and in other embodiments from 6 cm to 30 cm longer than membrane 112, although there is no limit to the length other than practical convenience. A person or ordinary skill in the art will recognize that additional ranges of length within the explicit ranges above are contemplated and are within the present disclosure.

Gentle traction on the "pull string", deforms the inner ring, and makes the diameter of the smaller dimension of the ring smaller, so making it simpler to pull through the stoma, and removing the entire device from the stoma, without trauma or pressure on the bowel. If the "pull string" or teter is deployed within the sleeve membrane, this ensures the inner ring is released and "pulled through" the inner lumen of the device, so potentially causing less pain to the patient. If the tether is located outside the inner and outer rings and the membrane, the tether would not interact with feces so the tether can remain cleaner, which would provide an advantage for this configuration. Referring to FIG. 15, engagement of cord 113 positioned outside of membrane 112 is used to disengage inner ring 111 from stoma 115 extending from abdominal wall 116. Referring to FIG. 16, removal of the device is shown using a pull string 113 passing through the interior of the membrane 112.

In a further embodiment, the rings may be expandable, using an inner spring located within the hollow lumen of the inner ring, which allows the ring to expand and contract. In another configuration, the inner ring may be expandable wherein the ring is discontinuous, or cut in a radial direction. One end of the cut ring is thinner and can be inserted into the wider end so expandable, in a similar manner as a snake swallowing its own tail. With respect to the inflatable embodiment of FIG. 8B, deflation of inner ring 101 allows for easy removal of the device by pulling on outer ring 20 or a tether.

The device is therefore a self-retaining endo-luminal device which avoids the need for conventional stoma plates and glues. The outer ring makes a stable platform where colostomy bags or occlusive plates or irrigation devices may be secured. This avoids the need for adhesive plates, glues, and powders. Since the lumen is an endoluminal device, no external plate is required and excoriation, inflammation or ulceration of the skin around the stoma is avoided.

Referring to FIG. 17, an embodiment of a colostomy bag 51 is shown having a fastener 52 for attachment to an outer ring of the ostomy device described herein. Fasteners 52 can have an appropriate design for secure attachment to the outer ring. Colostomy bag 51 can have a drainable design or be close with an intention of replacement when sufficiently full. Drainable ostomy pouches are described for example in U.S. Pat. No. 9,011,395 to Friske et al., entitled "Drainable Ostomy Pouch," and in published U.S. patent application 2017/0209297 to Lysgaard, entitled "A Drainable Collection Bag," both of which are incorporated herein by reference.

Referring to the insert of FIG. 17, the ostomy device can comprise a wafer-type structure 120 having a flange 121 for a snap fit to a colostomy bag 51 and fasteners 122 for attachment to an outer ring or as an alternative to the outer ring. The left view of the insert depicts the outer surface of wafer-type structure 120 and the right view depicts the inner surface of wafer-type structure 120. Having a wafer-type structure attached to the ostomy device still avoids the securing of a wafer to the patient's abdomen using adhesives, but can provide more familiar faster designs for securing an ostomy bag. Also, such a wafer can distribute some weight from the bag to the patient's abdomen without the need for adhesives and while avoiding irritation to the patient's skin due to possible contact with stool.

Figure 18A:
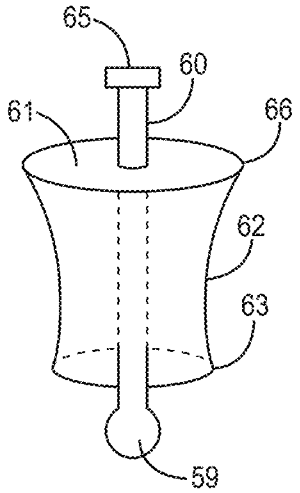
FIG. 18A is a perspective view of an endoluminal stoma channel with an inflatable plug positioned adjacent to and past the inner ring.
Figure 18B:
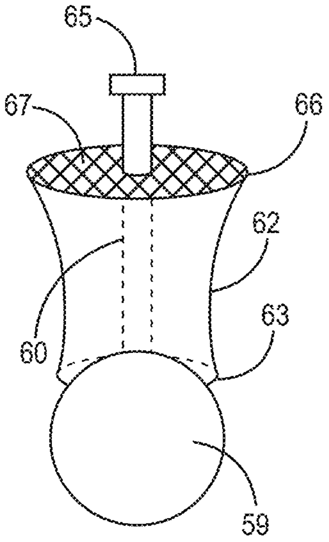
FIG. 18B is a perspective view of the devices of FIG. 18A with the plug inflated and positioned to block entry into the inner ring from the bowel.

Referring to FIG. 18A, in a further embodiment, an inflatable balloon is 59 provided, attached to a fluid conduit 60, which is inflated in a similar manner as the balloon on a Foley catheter. The deflated balloon is inserted through the lumen 61 of the deployed device 62 and positioned further within the patient's abdomen past the inner ring 63 of the deployed device. The balloon 59 is then inflated with fluid via the fluid conduit 60, as depicted in FIG. 18B. The Fluid conduit has a valve 65 such as a Luer Lock fitting which maintains pressure within the balloon and prevents leakage from the balloon 59.

Figure 19C:
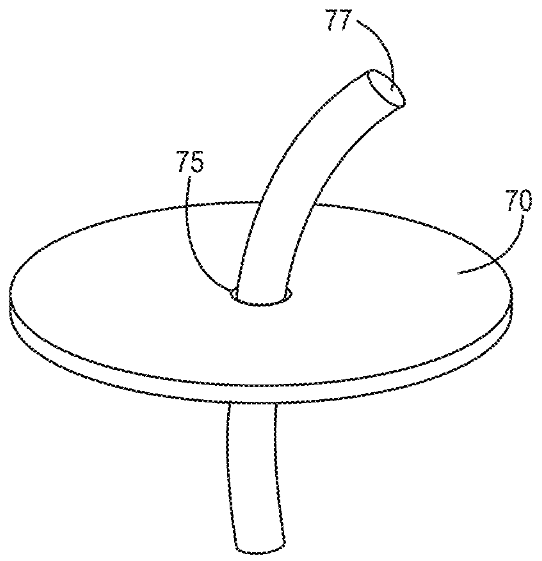
FIG. 19C is a perspective view of the cap of FIG. 1A with a drain tube extending through the valve.

Referring to FIG. 18B, the inflated balloon 59 is pulled gently toward the inner ring 63 of the device and forms a seal between the inflated balloon and the inner ring of the device, similar to a "Ball valve" device. The inflated balloon prevents stool, liquid and gas from exiting through the device and creates a stable mechanical seal between the balloon and the inner ring. The inflatable fluid conduit may be secured at the outer ring 66 or a plate or the like 67 attached to the outer ring by a slot or key-hole type configuration which secures the balloon at the inner ring 63 and maintains the seal between the balloon and the inner ring An occluding plate/cover or cap which is attached to the outer ring may take several forms. In one embodiment shown in FIG. 19A, the cap 70 is a circular "clip-on" device which is detachably attached to outer ring 71 using clips or snaps 72. In a further embodiment, cap 70 performs as an occluding member and comprises a hinged disc or plate 73, with is detachably or non-detachably affixed to outer ring 71 at hinge 74. The terms plate, cover or cap can be used essentially interchangeably unless some specific meaning follows from the context. The hinged member can have a circular shape, with hinge 74 located at the circumference of the plate 73, and can be opened and closed, like a "port-hole" in a ship. In a further embodiment, the occluding member, such as cap 70, comprises a valve 75, which can have a plurality of "leafs", as shown in FIG. 19A. The valve prevents stool gas and liquid from leaking from the device, but allows the patient to insert an object such as an irrigating tube into the stoma, to irrigate the colostomy. An irrigating tube 77 inserted through valve 75 is shown in FIG. 19C. The valve may have 2 leafs, such as the mitral valve in the heart, or three leafs, such as the tricuspid valve in the heart, or a plurality of leafs. Cap 70 can also have a vent 76 in some embodiments. Vent 76 (FIG. 19A) can be open for passage of gas, and/or a releaseable cover for selective release of gas, and vent 76 may have a filter, such as a charcoal filter, through which the gas can pass.

In a further embodiment, the occluding device incorporates a "gel" disc, similar to the commercially available "Gel Port" device (Applied Medical) used for laparoscopic abdominal surgery, and such gel disc products have been well described in the literature, see U.S. Pat. No. 7,736,306 and US 2020/0008792 to Becerra et al., entitled "Mechanical Gel Surgical Access Device," both of which are incorporated herein by reference. The gel is a viscous, deformable jelly material which maintains its shape even when an object is inserted through the gel. Insertion is facilitated by a "cross-hairs" incision incorporated in the center of the gel. In this embodiment, a gel disc is detachably attached to the outer ring of the stoma device, and can be used to access the lumen of the colon, via the device. The gel disc prevents leakage of stool liquid of gas from the colostomy, but permits the insertion of objects such as drainage tubes. Such drainage tubes can be used to irrigate the colon, to empty it, or to drain accumulated fluids, such as in an ileostomy. The gel disc avoids the need to detach and reattach other occluding devices such as discs, plates, hinges plates, snap-on discs, clamp-on discs, ball valve devices, or valve devices.

In a further embodiment, the patient may wish to personalize the surface of the occluding member. Option may include a skin colored surface to match the patients skin color. Other possibilities include light hearted shapes or art such as hearts, cartoon characters, or "no entry" signs.

In practice, the ostomy device can be used for an extended period of time or replaced at a recommended period, such as daily, weekly, monthly or other appropriate period. To this end, the device can be designed to be inserted and removed by a physician, an ostomy nurse, other health care profession or the patient themselves. Generally, the ostomy bag is emptied and/or replaced by the patient or a care provider on a time frame generally of multiple times a day on average.

Long Term Use/Biocompatible Material

Commercial devices such as the "Alexis" retractor is designed for short term use (typically 1-2 hours) as an abdominal wall retractor during surgical laparotomy, or as a skin retractor, as during breast biopsies. The membrane material is designed for contact with the patients tissue for just the duration of the surgical procedure, for instance several hours, but no longer than 24 hours.

In the current devices, components of the device can remain in place for a much longer period of time, and the membrane and ring material can be biocompatible with the patient's tissues for days, or weeks. A patient with a prior art colostomy typically changes the palate 2 or 3 times a week, to avoid skin irritation, or fungal or bacterial overgrowth. With the current system, the device may be changed every week or two, or only when problems arise, such as dislodgement of the device or leakage from the device. This longer term contact with the patient's tissues can suggest the selection of a longer-term biocompatible material for the rings and sleeve components. Suitable polymers include, for example, polyamides (e.g., nylon), polyesters (e.g., polyethylene teraphthalate), polyacetals/polyketals, polyimide, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, natural and synthetic rubbers, similar copolymers and mixtures thereof. Suitable metals can include, for example, titanium, stainless steel, and alloys such as Nitinol and other spring metals.

Often patients with colostomies irrigate the stoma once a day, to empty the colon of liquid, gas and stool. After irrigating, these patients typically apply a large "bad-aid" device over the stoma, to conceal the stoma, and minimize leakage. The current device allows for irrigation of the colon on a daily basis, and the occluding device (Plate, trapdoor, cap, gel-cap, valve or ball valve) is reapplied to prevent leakage.

Commercial retractors such as the Alexis retractor are designed to provide access to the abdominal cavity, Uterus (in Ceserian Sections) or skin, such as in breast biopsies, but these devices are not designed for longer term use or secure attachment to the patient away from supervision by a health care professional. The current system and associated device components has a plurality of designs and functions. A major function is to occlude a stoma and prevent leakage of stool gas and liquid. Various mechanisms are described herein which accomplish this: Using the ball-valve, hinged-plate, snap-on, a simple cap, screw on, gel-cap, or valve occluding devices. This function is distinct from vaguely similar commercial devices, which are designed to open access into a body cavity. A further function is to create a stable platform to attach colostomy bags, and to avoid the use of prior art colostomy plates and adhesives.

Patient Experience

Figure 20:
FIG. 20 is a photograph of a patient's stoma and abdomen prior to placement of an endoluminal stoma channel.

A 57 year old morbidly obese male underwent a "Hartman's resection" for perforated diverticulitis. After multiple post-operative complications including sepsis, respiratory and cardiac failure, he survived but was hospitalized for over a month. Because of his obesity, and a 5 in deep abdominal wall, the end of the colostomy underwent ischemic necrosis, leaving a pencil thin "blow-hole+fistula (FIG. 20). This resulted in severe back-up of stool, causing severe abdominal pain, and persistent problems "pouching" the stoma, due to the patient's body habitus. The device was inserted into the "blow-hole" colostomy and deployed in the stoma, forming a stable platform for placement of a colostomy bag (FIG. 21). The device remained in place and even applying significant traction to the device failed to dislodge the device (FIG. 22). The patient underwent a successful bowel prep to clean out the colon, and had surgery to reverse the colostomy, and re-anastomose the colon to the rectum.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. To the extent that specific structures, compositions and/or processes are described herein with components, elements, ingredients or other partitions, it is to be understand that the disclosure herein covers the specific embodiments, embodiments comprising the specific components, elements, ingredients, other partitions or combinations thereof as well as embodiments consisting essentially of such specific components, ingredients or other partitions or combinations thereof that can include additional features that do not change the fundamental nature of the subject matter, as suggested in the discussion, unless otherwise specifically indicated.

What is claimed is:

1. An endoluminal stoma channel comprising:

an inner ring that is resilient and deformable;

an outer ring;

a flexible polymer sleeve connected to the inner ring and the outer ring to form a flow channel and comprising a biocompatible polymer;

wherein the flexible polymer sleeve is connected to the outer ring such that the outer ring can be rolled over to shorten the flexible polymer sleeve; and a tether comprising a cord and a knob, wherein the cord is attached to the inner ring, and the knob has a position such that the cord can extend along the sleeve, in the interior or adjacent the exterior of the sleeve, past the outer ring with the outer ring pulled away from the inner ring such that the sleeve is taut.

2. The endoluminal stoma channel of claim 1 wherein the inner ring comprises an elastomeric polymer.

3. The endoluminal stoma channel of claim 1 wherein the outer ring has a larger diameter than the inner ring.

4. The endoluminal stoma channel of claim 1 wherein the outer ring comprises an elastomeric polymer and has a non-circular cross section.

5. The endoluminal stoma channel of claim 1 wherein the inner ring and the outer ring independently have diameters from 1-10 cm, and the sleeve has a length from 5-20 cm.

6. The endoluminal stoma channel of claim 1 wherein the flexible polymer sleeve is connected to the inner ring and/or the outer ring through adhesive bonding or heat bonding.

7. The endoluminal stoma channel of claim 1 wherein the outer ring comprises a split ring configuration.

8. The endoluminal stoma channel of claim 1 wherein the inner ring is deformable into a figure of 8 and returns to an un-deformed state after being deformed.

9. The endoluminal stoma channel of claim 1 wherein the endoluminal stoma channel is self-retaining when secured around a stoma.

* * * * *